US012805743B2

(12) United States Patent
Zhang

(10) Patent No.: US 12,805,743 B2
(45) Date of Patent: Nov. 24, 2026

(54) METHOD AND DEVICE FOR MAGNETIC RESONANCE IMAGING PRE-SCAN, AND MAGNETIC RESONANCE IMAGING SYSTEM

(71) Applicant: Siemens Healthineers AG, Erlangen (DE)

(72) Inventor: Qiong Zhang, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 620 days.

(21) Appl. No.: 18/131,459

(22) Filed: Apr. 6, 2023

(65) Prior Publication Data

US 2023/0320613 A1 Oct. 12, 2023

(51) Int. Cl.
*A61B 5/055* (2006.01)
*G01R 33/48* (2006.01)
(Continued)

(52) U.S. Cl.
CPC .......... *A61B 5/055* (2013.01); *G01R 33/4818* (2013.01); *G01R 33/543* (2013.01); (Continued)

(58) Field of Classification Search
CPC ................ A61B 5/055; G01R 33/4818; G01R 33/5608; G01R 33/5614; G01R 33/56563; G01R 33/543
See application file for complete search history.

(56) References Cited

U.S. PATENT DOCUMENTS

2005/0165295 A1 7/2005 Li et al.
2010/0045291 A1* 2/2010 Greiser .................. G01R 33/58 324/309
(Continued)

FOREIGN PATENT DOCUMENTS

EP 3805776 A1 4/2021

OTHER PUBLICATIONS

Tang, Yu-Wei et al: "Fast and Fully Automatic Calibration of Frequency Offset for Balanced Steady-State Free Precession Cardiovascular Magnetic Resonance At 3.0 Tesla"; Journal of Cardiovascular Magnetic Resonance, Biomed Central Ltd, London UK, vol. 15, No. 1; published: Apr. 11, 2013.

*Primary Examiner* — Rishi R Patel
(74) *Attorney, Agent, or Firm* — Banner & Witcoff, Ltd.

(57) ABSTRACT

Techniques for MRI pre-scan method may automatically determine and apply a compensation frequency to correct for inhomogeneous magnetic fields, improving the efficiency and quality of clinical examinations. The method may include executing a first pulse sequence with an MRI system, acquiring multiple magnetic resonance signals at different offset frequencies from the same location, and recording corresponding k space data. Variations between the k space data may be calculated and used to determine the compensation frequency. By applying the compensation frequency to correct for inhomogeneous magnetic fields, artifacts in MRI images can be eliminated, resulting in higher quality images. This method offers a quantitative and automated solution for compensating for inhomogeneous magnetic fields during MRI pre-scans, improving the accuracy and efficiency of clinical examinations. The invention also includes a dedicated MRI pre-scan device. The system and method have broad applications in the field of medical imaging.

23 Claims, 6 Drawing Sheets

(51) Int. Cl.

| | |
|---|---|
| ***G01R 33/54*** | (2006.01) |
| ***G01R 33/56*** | (2006.01) |
| ***G01R 33/561*** | (2006.01) |
| ***G01R 33/565*** | (2006.01) |

(52) U.S. Cl.
CPC ..... *G01R 33/5608* (2013.01); *G01R 33/5614* (2013.01); *G01R 33/56563* (2013.01)

(56) References Cited

U.S. PATENT DOCUMENTS

| | | | | |
|---|---|---|---|---|
| 2017/0358095 | A1* | 12/2017 | Levy | G01R 33/4808 |
| 2018/0067176 | A1* | 3/2018 | Weingartner | G01R 33/385 |
| 2023/0122915 | A1* | 4/2023 | Nehrke | G01R 33/5608 702/85 |

* cited by examiner

METHOD AND DEVICE FOR MAGNETIC RESONANCE IMAGING PRE-SCAN, AND MAGNETIC RESONANCE IMAGING SYSTEM

CROSS REFERENCE TO RELATED APPLICATIONS

This patent application claims priority to Chinese Patent Application No. 202210353609.1, filed Apr. 6, 2022, which is incorporated herein by reference in its entirety.

BACKGROUND

Field

The present disclosure relates to the field of medical imaging, and in particular to a method and a system for magnetic resonance imaging pre-scan with the aid of a magnetic resonance imaging pre-scan with the aid of a magnetic resonance imaging system.

Related Art

Magnetic resonance imaging (MRI) is a medical imaging technique in which an antenna is used to irradiate an object with radio frequency pulse signals under certain magnetic field conditions, and images are generated on the basis of modulated radio frequency signals received from the object. MRI technology can be used to study the internal structure, composition and physiological processes, etc., of the object. A radio frequency pulse with Larmor frequency causes spin nucleons, such as hydrogen nuclei (that is, H+), in the irradiated object to precess at a deflection angle, and, after excitation, a magnetic resonance radio frequency signal is generated, which is received by a radio frequency antenna unit and then processed by a computer to generate an image.

In some clinical applications, an MR imaging system executes clinical scanning protocols on pulse sequences, such as balanced Steady State Free Precession (SSFP) sequences and True Fast Imaging Steady State Precession (TrueFISP or TRUFI) sequences, for medical imaging or spectral analysis. A balanced SSFP (also known as SFP or bSSFP) sequence is a magnetic resonance imaging sequence that constructs balanced magnetic field gradient waveforms and applies steady-state magnetic fields. Balanced SSFP sequences are usually based on a low-flip-angle gradient-echo sequence with a short repetition time. The image contrast achieved with balanced SSFP sequences mainly depends on the repetition time (TR—the time interval between two consecutive applications on the same layer of pulse sequences), the relaxation time and the flip angle, while balanced SSFP sequences are susceptible to off-resonance artifacts caused by an inhomogeneous magnetic field. Before executing a relevant clinical scanning protocol, an MR imaging system usually executes a frequency scanning protocol to determine an offset frequency as the compensation frequency for eliminating off-resonance artifacts. After the MR imaging system executes a frequency scout protocol to obtain a plurality of corresponding images, an operator needs to identify, from the images, an image with the best quality, and uses the offset frequency corresponding to the known offset frequency as the compensation frequency, so that dynamic shimming, for example, may be performed. However, manual assessment of image quality by an operator is not based on quantitative analysis and may contain a considerable error and takes a lot of time.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
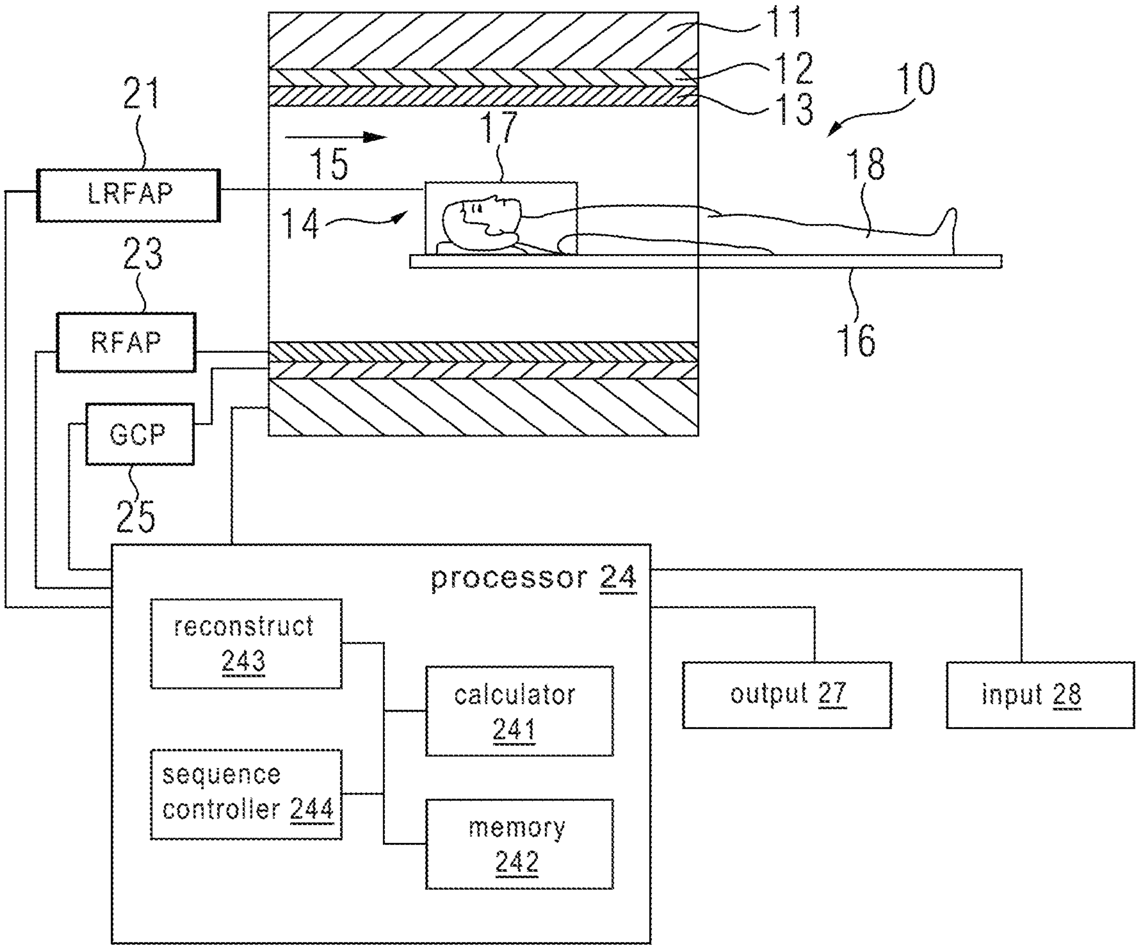
FIG. 1 is a magnetic resonance imaging system according to one or more exemplary embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

In view of the above-mentioned problems, the present disclosure, on the one hand, proposes a method of magnetic resonance imaging pre-scan by means of a magnetic resonance imaging system, which makes it possible to automatically and quantitatively determine an offset frequency, and, on the basis of the offset frequency, apply an electrical signal to a radio frequency antenna unit that generates a magnetic field, so as to compensate for an inhomogeneous magnetic field. The method comprises the steps of: executing a first pulse sequence by means of a magnetic resonance imaging system, acquiring, by a radio frequency antenna unit, a plurality of magnetic resonance signals at different offset frequencies at one same location from an object, and recording the corresponding first k space data on the basis of a plurality of magnetic resonance signals; calculating variations between the plurality of pieces of first k space data respectively; and determining, according to variations, an offset frequency as the compensation frequency for compensating for an inhomogeneous magnetic field.

Another aspect of the present disclosure provides a magnetic resonance imaging pre-scan device for magnetic resonance imaging, the device comprising: a processor configured to execute a first pulse sequence by means of a magnetic resonance imaging system, acquire, by a radio frequency antenna unit, a plurality of magnetic resonance signals at different offset frequencies at the same location from an object, and record the corresponding first k space data on the basis of a plurality of magnetic resonance signals; and a calculating unit configured to respectively calculate variations between the plurality of pieces of first k space data, and determine, according to the variations, an offset frequency as the compensation frequency for compensating for an inhomogeneous magnetic field.

Another aspect of the present disclosure provides a magnetic resonance imaging system configured to implement the method described above.

Another aspect of the present disclosure provides a computer-readable storage medium on which a program segment readable and operable by the magnetic resonance imaging pre-scan device is stored, so that when the program segment is run by the magnetic resonance imaging pre-scan device, all the steps of the method described above may be executed.

One advantage of the magnetic resonance imaging pre-scan method, the magnetic resonance imaging system, and the computer-readable storage medium provided by the present disclosure is the ability to analyze variations between a plurality of magnetic resonance signals acquired by the magnetic resonance imaging system during the execution of a first pulse sequence, which makes it possible to automatically and quantitatively determine an offset frequency, and the information about the offset frequency may be used to generate an electrical signal acting on a radio frequency antenna unit to compensate for an inhomogeneous magnetic field and eliminate artifacts caused by the inhomogeneous magnetic field, thereby improving the quality and efficiency of the execution of pulse sequences of a clinical examination by the magnetic resonance imaging system.

Balanced Steady State Free Precession (SSFP) sequences, True Fast Imaging Steady State Precession (TrueFISP or TRUFI) sequences, and other pulse sequences are widely used in clinical diagnosis and imaging with nuclear magnetic resonance due to their good contrast and high signal-to-noise ratio signals. However, TRUFI sequences are highly sensitive to inhomogeneous magnetic fields, which results in off-resonance artifacts. The above-mentioned artifacts are particularly serious in a higher (for example, 3T or higher) magnetic field. Therefore, before running a general TRUFI sequence, it is necessary to perform a frequency scout (acquisition) to define off-resonance frequency. Then, an operator needs to check all the images obtained by a frequency scout and manually select an offset frequency according to the image with the best quality among the images for use as the compensation frequency for compensating for an inhomogeneous magnetic field. For example, the frequency scout protocol (such as TRUFI sequence) running before a conventional MRI clinical scanning protocol is executed to scan the same layer or location by setting step offset frequencies, and compares the images obtained at different offset frequencies to determine an appropriate offset frequency for use as the compensation frequency for compensating for an inhomogeneous magnetic field.

Considering the above-described factors, the present disclosure provides a data acquisition method, which allows for automatically defining the most suitable offset frequency for use as the compensation frequency on the basis of the images obtained by frequency scouting or sweep frequency, thus making it simpler and more efficient to acquire data using balanced SSFP-compatible sequences, such as TRUFI sequences.

FIG. 1 is a schematic diagram of a magnetic resonance imaging system of an exemplary embodiment.

Referring to FIG. 1, an MR imaging system 10 is described, and with this magnetic resonance imaging system 10, the method of acquiring data on a magnetic resonance image of an object 18 may be executed. In the MR imaging system 10, the magnet 11 is configured to generate a static $B_0$ magnetic field 15 to image the object 18, and the object 18 is placed on a scanning table to adjust the location thereof in the scanning space. The MR imaging system 10 comprises a gradient coil unit 12 for generating a location-related gradient magnetic field superimposed on the $B_0$ magnetic field 15, and a sequence processor 244 is configured herein to, in response to receiving a gradient signal, generate location-related magnetic field gradients in three orthogonal directions and generate a pulse sequence comprising a balanced SSFP-compatible pulse sequence (for example, a TRUFI pulse sequence). A magnetic field gradient comprises a gradient magnetic field selected for a layer (or slice), a phase-coded gradient magnetic field, and a read gradient magnetic field to act on the object. Further, the radio frequency (RF) antenna controller 23 is configured to provide the radio frequency antenna unit 13 with an alternating magnetic field with certain parameters (that is, an RF pulse signal), which is used to, in response to a generated magnetic field pulse, flip the proton spin in the body of the object by an angle of 90° or 180° to obtain an image of spin echo, or by an angle of smaller than or equal to 90° to obtain an image of gradient echo. The sequence controller 244 is combined with the radio frequency antenna controller 23 to be configured to be under the control of the processor 24, so as to control layer selection, phase coding, reading of a gradient magnetic field, transmission of an RF pulse signal, and detection of a magnetic resonance signal, thereby obtaining a magnetic resonance signal representing the plane layer of the object.

In response to the application of an RF pulse signal, the radio frequency antenna unit 13 receives a magnetic resonance signal returned from the object 18, which means that excited-state protons in the body of the object 18 go into the equilibrium state again under the action of both the static $B_0$ magnetic field 15 and the gradient magnetic field to realize spin reunion, thus generating a magnetic resonance signal. The magnetic resonance signal is received by the RF antenna unit 13 and processed in the RF antenna controller 23, for example, through analog-to-digital signal conversion and low-noise amplification processing, the image representation data, such as k space data, is transmitted to the processor 24, and the image is reconstructed by means of the reconstruction unit 243 with image processing functions that is associated with its calculating unit 241. In addition, the local radio frequency antenna 17 is usually arranged in a region of interest of the object and can also send an RF pulse signal to the object in response to an RF pulse signal, which is received and processed by means of the local radio frequency antenna controller 21. A magnetic resonance signal detected by each RF antenna unit 13 is associated with a corresponding MR measurement channel. The general operating modes used to generate MR images and detect MR signals are not further described here.

The memory 242 included in the processor 24 comprises, for example, storable information, including preset pulse sequences, RF pulse signals/sequences, magnetic field gradient sequences, and preset parameters such as intensity data, time sequences, orientation, and spatial volume of gradient magnetic field acting on imaging, as well as procedures for the operation of the MR imaging system 10. The processor 24 controls the gradient magnetic field and RF pulse sequence as well as the interval of receiving magnetic resonance signals as a function of determined pulse sequences. The magnetic resonance image displayable on the display unit 27 is calculated in the calculating unit 241, and the display unit 27 can display a graphical user interface (GUI) to facilitate interactions between a user and the processor 24 and allow the user to perform operations, wherein the user operates the MR imaging system 10 by the input unit 17. The memory 242 may be provided with imaging sequences (or pulse sequences) and program modules, wherein one of the program modules comprises a program directly loadable into the memory 242 of the programmable calculating unit 241 of the processor 24, so that when the program is implemented in the calculating unit 241 of the processor 24, the pulse sequences, the magnetic field gradient sequences, and the instruction included in the program are implemented to perform the magnetic resonance imaging pre-scan method of the present disclosure. In an exemplary embodiment, the processor 24 may include processing circuitry that is configured to perform one or more functions and/or operations of the processor 24. The processor 24 may be referred to as a controller in one or more aspects, and the processor 24 may be configured to control the operation of the MR imaging system 10 (including one or more components therein). In an exemplary embodiment, one or more components of the processor 24 may include processing circuitry that is configured to perform one or more respective functions and/or operations of the component(s).

Figure 2:
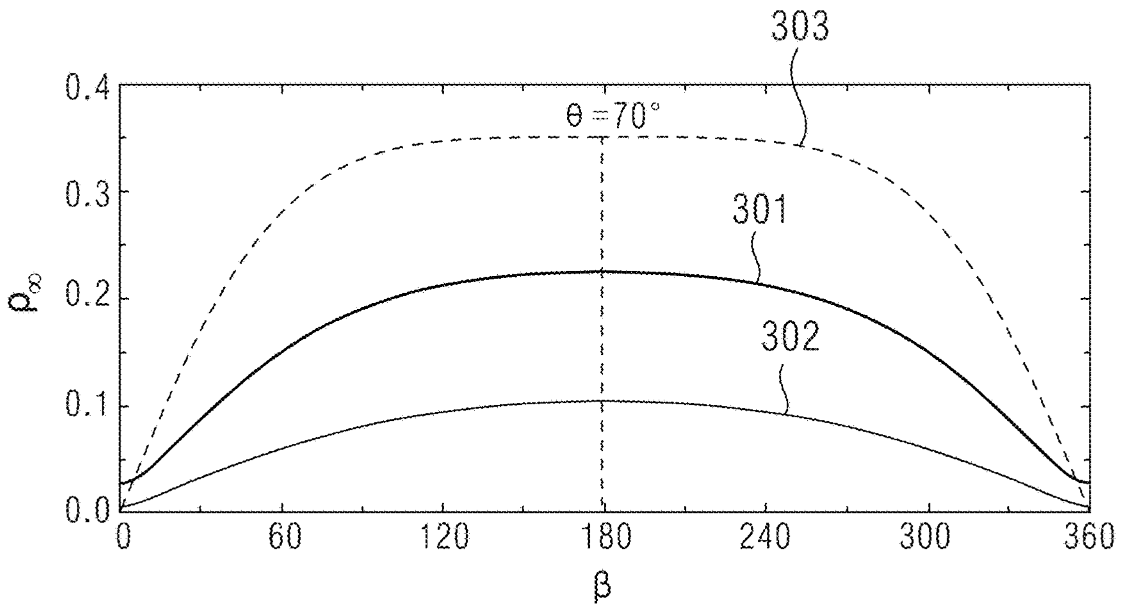
FIG. 2 is a plot of a spectral response function of balanced SSFP pulse sequences according to one or more exemplary embodiments.

As shown in FIG. 2, the curves in the chart show that the application can produce a flip angle θ for the protons in the body of the object under TRUFI imaging pulse sequences, and that according to the steady-state spectral response function presented by different anatomical substances, the curves may be obtained at a flip angle θ=70°, wherein the y-axis (longitudinal axis) is the transverse magnetization function $\rho_\infty$, the transverse magnetization function $$\rho_\infty = M_x^+ + iM_y^+$$

is defined as an approximation of anatomical material signal, and the curves of steady-state spectral response function exhibit the characteristics of a steady-state magnetic field. The x-axis (horizontal axis) is β, representing the phase angle of resonance (having a value in the range of 0-360 degrees), and the β midpoint is set at 180°. The curves, respectively based on the above-mentioned pulse sequences and variable flip angles θ and β, trace the signals of different anatomical substances, that is, the steady-state spectral response function presented, wherein anatomical substances, for example, include gray matter, fat and cerebrospinal fluid (CSF), and the corresponding gray matter steady-state spectral response curve 301, the fat steady-state spectral response curve 302, and the cerebrospinal fluid steady-state spectral response curve 303 are plotted. Total phase angle β(TR) can represent the accumulation of a local inhomogeneous magnetic field ΔB and a gradient field (or transverse magnetic field) $\vec{G}(t)$ between two consecutive excitations, namely $$\beta(TR) = \gamma\Delta B \cdot TR + \gamma\vec{r} \cdot \int_0^{TR} \vec{G}(t)dt,$$

wherein TR represents the repetition time, that is, the length of time between two excitations, and γ is the gyromagnetic ratio. In addition, the offset frequency (ΔB) introduced by an inhomogeneous magnetic field may be expressed as Δf=ΔB, which can determine an offset frequency, and, at the offset frequency, which is used as a compensation frequency, a received magnetic resonance signal is less affected by a magnetic field, so that the impact of an inhomogeneous magnetic field is reduced, and if artifacts or image distortions are introduced by an inhomogeneous magnetic field, the image quality of magnetic resonance imaging may be optimized, and then a pulse sequence with the compensation frequency is constructed to compensate for the inhomogeneous magnetic field and eliminate the artifacts introduced thereby.

Specifically, a TRUFI pulse sequence is a pulse sequence compatible with a free steady-state precession sequence, and the evolution of its pulse sequence signal may be represented by the following Bloch equation:

$$M_x^+(\infty) = M_x^-(\infty)$$

$$M_y^+ = M_0(1 - E_1)\frac{\sin\theta(1 - E_2\cos\beta)}{d}$$

$$M_z^+ = M_0(1 - E_1)\frac{[E_2(E_2 - \cos\beta) + (1 - E_2\cos\beta)\cos\theta]}{d}$$

In the equation, $E_2 = e^{-T_R/T_2}$;

$$d = (1 - E_1\cos\theta)(1 - E_2\cos\beta) - E_2(E_1 - \cos\theta)(E_2 - \cos\beta)$$

In the equation, $$E_1 = e^{-T_E/T_1}, \text{ and } M_x^+, M_y^+, M_z^+$$

are the magnetic fields in directions x, y and z, TE is the echo time, that is, the time interval between sending of an RF pulse signal to the object and return of an echo signal (that is, magnetic resonance signal) from the object; TR indicates the repetition time (or the time interval between successive excitations), T1 and T2 are relaxation parameters respectively, θ indicates the flip angle (of excited proton), and β indicates the phase angle of resonance, which will not be described in detail again herein.

The idea behind the present disclosure is to provide a magnetic resonance imaging pre-scan method, which allows the use of an MR imaging system, for example, to automatically analyze magnetic resonance signals, which are acquired after a frequency scout is performed, and the image data reconstructed on the basis of magnetic resonance signals, and the automatic analysis may be, for example, analyzing the variation relationship between adjacent image data and quantitatively determining an offset frequency for use as the compensation frequency for compensating for an inhomogeneous magnetic field, so that off-resonance artifacts caused by an inhomogeneous magnetic field when, for example, balanced SSFP pulse imaging sequences are executed, may be eliminated.

Figure 3:
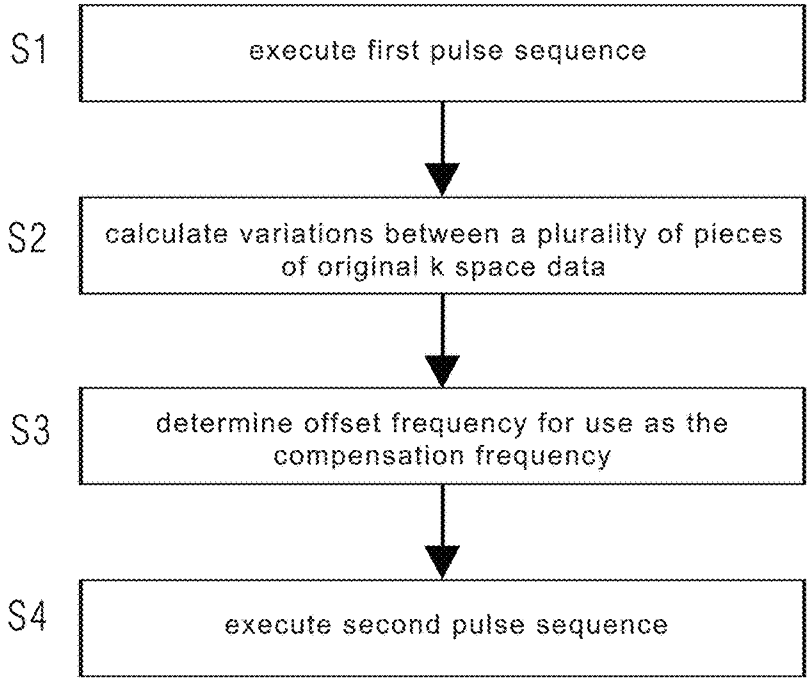
FIG. 3 is a flowchart of a method of magnetic resonance imaging pre-scan with the aid of a magnetic resonance imaging system according to one or more exemplary embodiments.

FIG. 3 is a flow diagram of a magnetic resonance imaging pre-scan method with the aid of a magnetic resonance imaging system according to an embodiment of the present disclosure.

Refer to FIG. 3, which shows schematically a method of magnetic resonance imaging pre-scan. In step S1, a first pulse sequence is executed by means of an MRI imaging system, and a plurality of magnetic resonance signals at the same location (or on the same layer) and different offset frequencies are acquired from the object through a radio frequency antenna unit, and the corresponding original k space data is recorded on the basis of the plurality of magnetic resonance signals, wherein the original k space data may be recorded in the matrix of the k space according to a certain trajectory. Here, the first pulse sequence may be implemented, wherein, for example, the first pulse sequence may serve as a frequency scout or provide magnetic field changes in frequency swing between acquiring single images for a set of image data about the anatomical region or volume of interest on the basis of a balanced SSFP pulse imaging sequence or a pulse imaging sequence compatible with a balanced SSFP pulse imaging sequence, for example, a TRUFI sequence, in a linear and frequency-based step (progressive shift) manner.

In step S2, variations between a plurality of pieces of original k space data are calculated respectively. In an illustrated embodiment, variations between one piece of the original k space data and the original k space data obtained at adjacent offset frequencies is calculated to obtain a plurality of variations corresponding to the k space data, wherein, for example, the k space data corresponding to the nth magnetic resonance signal may be expressed as $\text{signal}_n$, and the corresponding variation $\text{Var}_n$, for example, the amplitude variation, may be expressed as:

$$\text{Var}_n = \|\text{signal}_n - \text{signal}_{n-1}\|/2 + \|\text{signal}_n - \text{signal}_{n+1}\|/2.$$

Specifically, in an illustrated embodiment, the variation may comprise respectively calculating the sum of amplitude variations at a plurality of k space locations between one piece of original k space data and two pieces of original k space data obtained at adjacent offset frequencies, that is, $$\text{Var}_1(n) = \frac{1}{2}\left\|\sum_1^m P_{i_{(ksp_n)}} - \sum_1^m P_{i_{(ksp_{n-1})}}\right\| + \frac{1}{2}\left\|\sum_1^m P_{i_{(ksp_n)}} - \sum_1^m P_{i_{(ksp_{n+1})}}\right\|$$

In the equation, $\text{Var}_1(n)$ can indicate the sum of amplitude variations between the nth piece of original k space data and the original k space data obtained at the two adjacent offset frequencies at a plurality of k space locations [the k space data etc., representing the ith, (i−1)th, and (i+1)th points, namely, $P_{i(ksp_n)}$, $P_{i(ksp_{n-1})}$, $P_{i(ksp_{n+1})}$ to the mth point].

In addition, the calculation of variations may further comprise respectively calculating the sum of energy value variations at k space locations between one original piece of k space data and two original pieces of k space data obtained at adjacent offset frequencies, namely, $$\text{Var}_2(n) = \frac{1}{2}\sqrt{\left\|\sum_1^m P^2_{i_{(ksp_n)}} - \sum_1^m P^2_{i_{(ksp_{n-1})}}\right\|} + \frac{1}{2}\sqrt{\left\|\sum_1^m P^2_{i_{(ksp_n)}} - \sum_1^m P^2_{i_{(ksp_{n+1})}}\right\|}$$

In the equation, $\text{Var}_2(n)$ can indicate the sum of energy value variations between the nth piece of original k space data and two pieces of original k space data obtained at the two adjacent offset frequencies at a plurality of k space locations [representing the ith, (i−1)th, and (i+1)th points, namely, $P_{i(ksp_n)}$, $P_{i(ksp_{n-1})}$, $P_{i(ksp_{n+1})}$, etc., to the mth point].

In step S3, according to variations, an offset frequency is determined for use as the compensation frequency for compensating for an inhomogeneous magnetic field. For example, the minimum variation is selected by comparing a plurality of variations calculated, and the offset frequency corresponding to the original k space data related to the minimum variation (corresponding to a magnetic resonance signal received by a radio frequency antenna unit at the offset frequency) is used as the compensation frequency for compensating an inhomogeneous magnetic field. This is because the original k space data corresponding to the minimum variation show that they are more consistent with the original k space data obtained at adjacent offset frequencies, and the offset frequency corresponding thereto may be used as the compensation frequency for compensating for an inhomogeneous magnetic field to eliminate artifacts, image distortions and other impacts introduced by an inhomogeneous magnetic field.

In step S4, by means of a magnetic resonance imaging system, a second pulse sequence is executed, and at least one radio frequency antenna unit gives a response to the second pulse sequence and applies the compensation frequency to configure an electrical signal to compensate for the inhomogeneous magnetic field. Here, the second pulse sequence, as a clinical examination or diagnosis pulse sequence, comprises a balanced SSFP (bSSFP) pulse sequence or a True Fast Imaging Steady State Precession (TRUFI) pulse sequence to obtain a magnetic resonance image or picture of the object.

Figure 4:
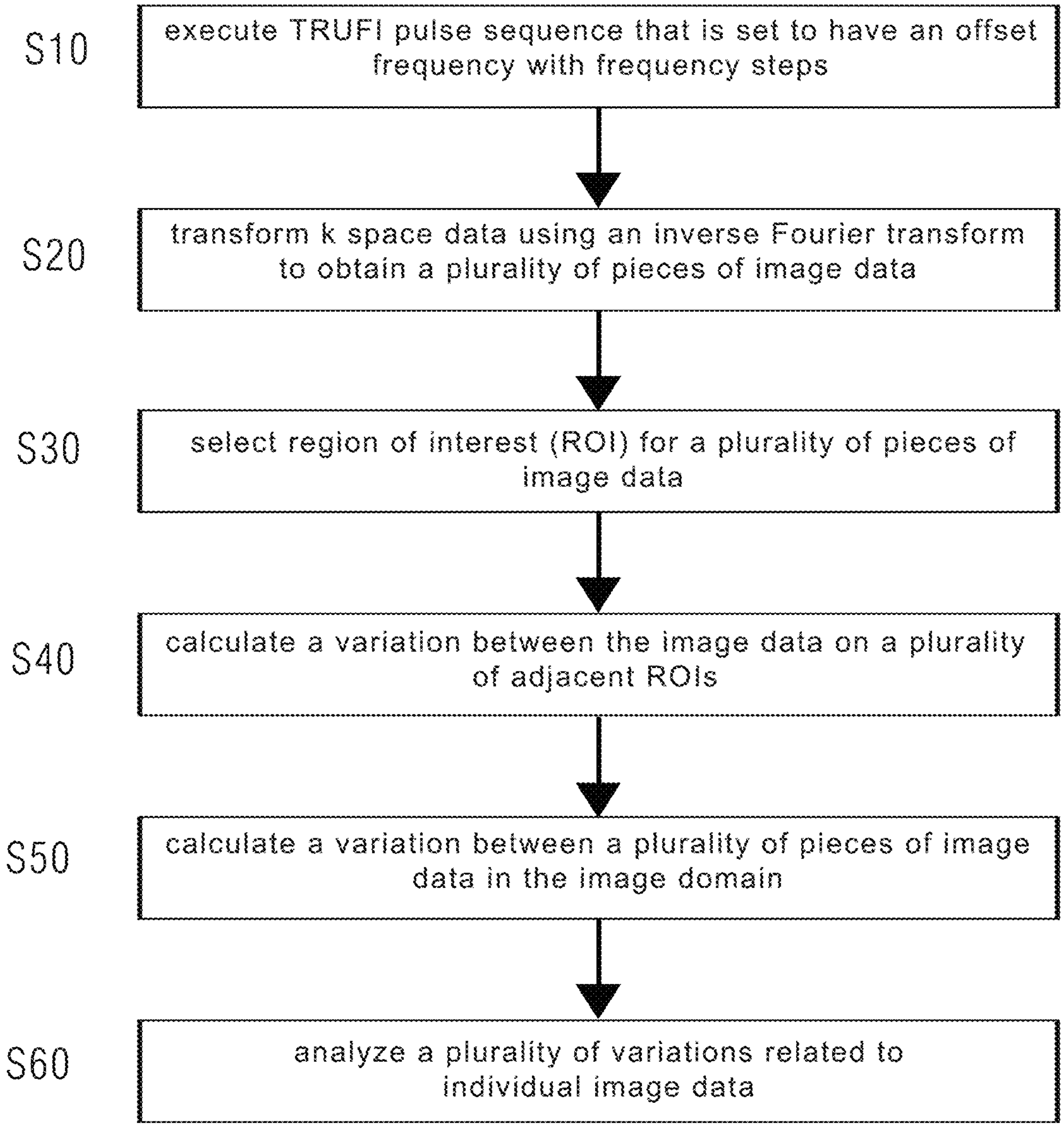
FIG. 4 is a flowchart of a calculation of variations based on image data to determine an offset frequency for use as the compensation frequency for compensating for an inhomogeneous magnetic field according to one or more exemplary embodiments.

FIG. 4 is a flow diagram of the calculation of variations on the basis of image data to determine an offset frequency for use as the compensation frequency for compensating for an inhomogeneous magnetic field in an exemplary embodiment.

Referring to FIG. 4, in an illustrated embodiment, in step S10, a TRUFI pulse sequence that is set to have an offset frequency with frequency steps is executed by means of a magnetic resonance imaging system, a plurality of magnetic resonance signals at the same location (on the same layer) are acquired from the object through a radio frequency antenna unit, and the corresponding original k space data is recorded on the basis of the plurality of magnetic resonance signals. Here, by means of a gradient coil unit and a radio frequency antenna unit, a TRUFI pulse sequence that is set to have an offset frequency with frequency steps, for example, may be executed, which means the same layer or the same location of the object is scanned, and a magnetic resonance signal of an echo from the same layer or location is acquired by a radio frequency antenna unit, wherein, for example, a layer is selected by the gradient coil controller to determine the magnetic resonance signal released from the same layer or the same location of the object, and a returned magnetic resonance signal is recorded in the k space (that is, in the k space matrix) with a certain trajectory, so as to obtain the original k space data.

In an illustrated embodiment, in order to construct a TRUFI pulse sequence so that it comprises an offset frequency with frequency steps, offset frequencies with frequency steps may be set successively in the gradient echo corresponding to a plurality of repetition times according to the time sequence of the TRUFI pulse sequence, for example.

In step S20, the k space data is transformed by means of inverse Fourier transform to obtain a plurality of pieces of image data. Here, a plurality of pieces of image data can sequentially correspond to offset frequencies with set frequency steps.

In step S30, a region of interest (ROI) is selected for a plurality of pieces of image data, a preset ROI area being generally a preset field of view (FOV).

In step S40, by calculating a variation between the image data on a plurality of adjacent, for example, ROIs, in an image domain, the variation comprising calculating the sum of the amplitude variations in voxels or pixels between one piece of image data and at least two pieces of image data obtained at adjacent offset frequencies, $$\mathrm{Var}_1(n) = \frac{1}{2}\left\|\sum_1^m P_{i_{(Imag_n)}} - \sum_1^m P_{i_{(Imag_{n-1})}}\right\| + \frac{1}{2}\left\|\sum_1^m P_{i_{(Imag_n)}} - \sum_1^m P_{i_{(Imag_{n+1})}}\right\|$$

In the equation, $\mathrm{Var}_1(n)$ can indicate the sum of amplitude variations in the pixels or voxels between the nth piece of image data and two pieces of image data at adjacent offset frequencies [represented as $P_{i(Imag_n)}$, $P_{i(Imag_{n-1})}$, $P_{i(Imag_{n+1})}$, etc.], and the nth piece of image data ($Imag_n$) can correspond to the sequence of offset frequencies with set frequency steps.

In step S50, a variation between a plurality of pieces of image data in the image domain is calculated, the variation comprising calculating the sum of energy value variations between one image data and the pixels or voxels at the corresponding locations of adjacent, for example, the preceding and the following image data, that is, for example, the sum of energy value variations between the corresponding points of the preceding and the following image data, $$\mathrm{Var}_2(n) = \frac{1}{2}\sqrt{\left\|\sum_1^m P^2_{i_{(Imag_n)}} - \sum_1^m P^2_{i_{(Imag_{n-1})}}\right\|} + \frac{1}{2}\sqrt{\left\|\sum_1^m P^2_{i_{(Imag_n)}} - \sum_1^m P^2_{i_{(Imag_{n+1})}}\right\|}$$

In the equation, $\mathrm{Var}_2(n)$ can indicate the sum of energy value variations in the pixels or voxels between the nth piece of image data and two pieces of image data at adjacent offset frequencies [represented as the ith, (i−1)th, and (i+1)th points, namely $P_{i(Imag_n)}$, $P_{i(Imag_{n-1})}$, $P_{i(Imag_{n+1})}$, etc.], and the nth piece of image data can correspond to the sequence of offset frequencies with set frequency steps. Note that it is possible to calculate a variation between image data by performing only step S40 or step S50.

In step S60, a plurality of variations related to individual image data are analyzed, and the magnitudes of the plurality of variations are compared to determine the minimum variation, so that the offset frequency corresponding to the image data is selected for use as the compensation frequency for compensating an inhomogeneous magnetic field. The offset frequency may function as a compensation frequency and is applicable to the configuration of an electrical signal, and an RF pulse signal generated by the radio frequency antenna unit in response to an electrical signal can comprise a compensation frequency for compensating for an inhomogeneous magnetic field. In an illustrated embodiment, by means of a magnetic resonance imaging system, a pulse sequence for diagnosis or clinical examination is executed, and the radio frequency antenna unit gives a response to the pulse sequence and applies the compensation frequency to configure an electrical signal, so that the radio frequency antenna unit irradiates the object with RF pulse signals.

Figure 5:
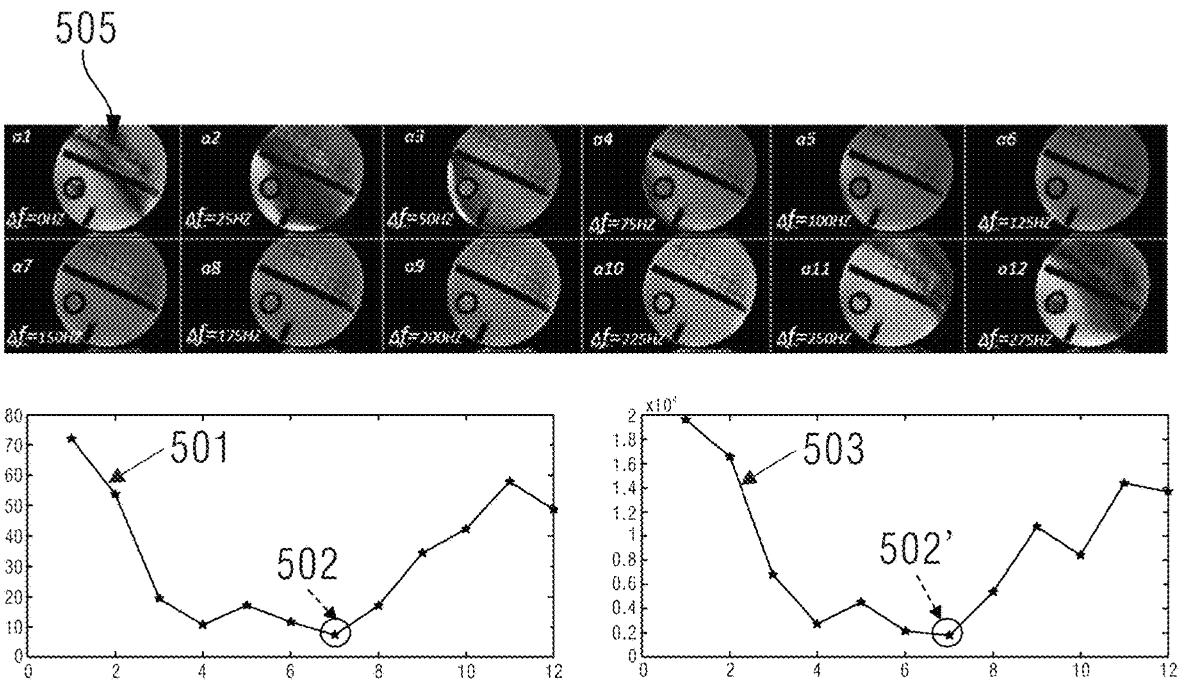
FIG. 5 shows curves of amplitude variations and energy value variations in an image domain between corresponding image data obtained by a phantom-based magnetic resonance imaging system in the execution of a pulse sequence including an offset frequency with a frequency step and image data obtained at adjacent offset frequencies according to one or more exemplary embodiments.

Referring to FIG. 5, a phantom-based magnetic resonance imaging system according to an exemplary embodiment executes a pulse sequence comprising an offset frequency with frequency steps and obtains the corresponding image data as well as the amplitude variation curve 501 and the energy value variation curve 503 of the image data obtained at adjacent offset frequencies in the image domain. The MR imaging system executes a TRUFI pulse sequence that is set to have an offset frequency Δf with frequency steps of 25 Hz to irradiate the same phantom (or the same location of the phantom) by a radio frequency antenna unit, which acquires magnetic resonance signals of a plurality of echoes, and the range of offset frequency Δf is set to be 0 Hz to 275 Hz and stepping at 25 Hz. The image reconstruction unit obtains 12 pieces of image data 505, which correspond to the image data 505 labeled a1 to a12 (a plurality of pieces of image data 505 correspond to labels a1, a2, . . . , a12, etc.), and the difference between the corresponding offset frequencies of the image data is 25 Hz (for example, the image data labeled a1 corresponds to the offset frequency 0 Hz, the image data labeled a2 corresponds to the offset frequency 25 Hz, and so on). After steps S40 and S50 are performed, the amplitude variation curve 501 and the energy value variation curve 503 corresponding to the image data 505 may be plotted respectively. In the amplitude variation curve 501, the sequence number of the image data 505 corresponding to the stepping offset frequency Δf is taken as the horizontal axis, and the sum of amplitude variations between each point of each piece of image data and the preceding and following image data 505 is taken as the vertical axis; in the energy value variation curve 503, the sequence number of the image data corresponding to the stepping offset frequency Δf is taken as the x-axis (horizontal axis), and the sum of the energy value variations between each point of each piece of image data and the preceding and following image data is taken as the y-axis (vertical axis). According to the amplitude variation curve 501, the sum of the amplitude variations of the 7th piece of image data is the minimum variation 502, and the sum of the energy value variations is the minimum variation 502', wherein the image quality of the 7th piece of image data is good (highly consistent with the minimum variation between the preceding and following image data), so the offset frequency Δf=150 Hz corresponding thereto may be selected for use as the compensation frequency for compensating for an inhomogeneous magnetic field.

Figure 6:
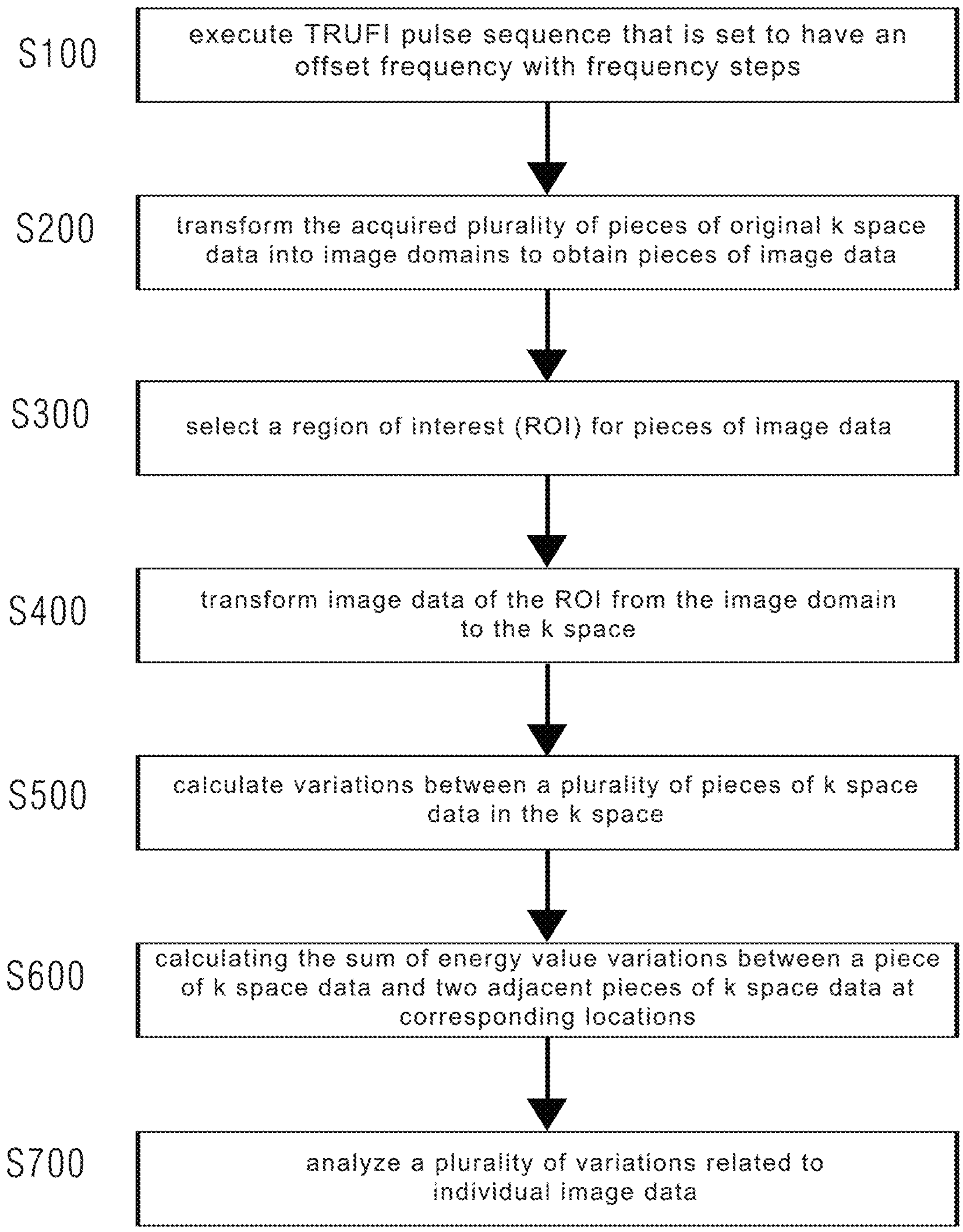
FIG. 6 is a flowchart of calculating variations based on k space data transformed from ROI image data to determine an offset frequency for use as the compensation frequency for compensating for an inhomogeneous magnetic field according to one or more exemplary embodiments.
Figure 7:
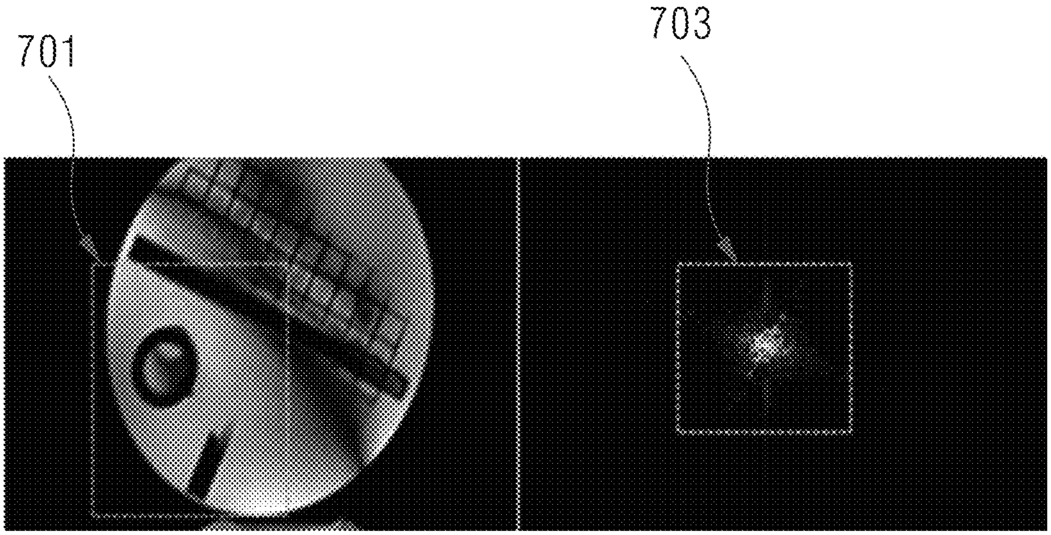
FIG. 7 shows regions of interest selected based on phantoms and corresponding k space data according to one or more exemplary embodiments.

Refer to FIG. 6, which further shows the flow of calculating variations on the basis of the k space data of the ROI image data transformation to determine an appropriate offset frequency for use as the compensation frequency for compensating for an inhomogeneous magnetic field. In step S100, by means of a magnetic resonance imaging system, a TRUFI pulse sequence that is set to have an offset frequency with frequency steps is executed, a plurality of magnetic resonance signals at the same location are acquired from the object by a radio frequency antenna unit, and the original k space data is recorded, wherein a phantom, for example, is selected as the object, and the scanning can focus on the same layer or location. Magnetic resonance signals are recorded in the k space with a certain trajectory, which may be Cartesian or non-Cartesian. In step S200, by means of inverse (multi-dimensional) Fourier transform, the acquired plurality of pieces of original k space data are transformed into image domains to obtain a plurality of pieces of image data, and the sequence of the image data can correspond to the offset frequency with set frequency steps, wherein, for example, as shown in FIG. 5, in the image data 505, the image data a1 corresponds to the offset frequency Δf=0 Hz, and the image data a12 corresponds to Δf=275 Hz. In step S300, a region of interest (ROI) is selected for a plurality of pieces of image data, wherein a plurality of pieces of image data are based on images acquired at the same layer or location. Refer to FIG. 7, which shows the region of interest 701 selected on the basis of the phantom and the corresponding window 703 region corresponding to the region of interest 701 in the k space, which means that the k space data in the window 703 region is obtained by changing the region of interest 701 from the image domain to the k space by means of multi-dimensional Fourier transform.

In step S400, the image data of the ROI is transformed from the image domain to the k space by means of (multi-dimensional) Fourier transform, and a plurality of pieces of k space data are obtained respectively, and the k space data comprises a plurality of points $P_1, P_2, \ldots, P_i, \ldots, P_m$ in the k space that may be rearranged.

In step S500, variations between a plurality of pieces of k space data in the k space are calculated respectively, the variations comprising respectively calculating the sum of amplitude variations at a plurality of k space locations between one piece of k space data and two pieces of k space data obtained at adjacent offset frequencies, that is, $$\mathrm{Var}_1(n) = \frac{1}{2}\left\|\sum_1^m P_{i(ksp_n)} - \sum_1^m P_{i(ksp_{n-1})}\right\| + \frac{1}{2}\left\|\sum_1^m P_{i(ksp_n)} - \sum_1^m P_{i(ksp_{n+1})}\right\|$$

In the equation, $\mathrm{Var}_1(n)$ can indicate the sum of amplitude variations between the nth piece of k space data and the preceding and following k space data at each k space location [representing the ith, (i−1)th, and (i+1)th points $P_{i(ksp_n)}$, $P_{i(ksp_{n-1})}$, $P_{i(ksp_{n+1})}$, etc.], and the nth piece of k space data can correspond to the nth piece of image data, that is, the sequence of offset frequencies with set frequency steps.

In step S600, calculating the variations comprises calculating the sum of energy value variations between one piece of k space data and two adjacent pieces of k space data at a plurality of corresponding locations, for example, the sum of energy value variations at each k space location (point) between at least two pieces of k space data, one of which immediately precedes the other, that is, $$\mathrm{Var}_2(n) = \frac{1}{2}\sqrt{\left\|\sum_1^m P^2_{i(ksp_n)} - \sum_1^m P^2_{i(ksp_{n-1})}\right\|} + \frac{1}{2}\sqrt{\left\|\sum_1^m P^2_{i(ksp_n)} - \sum_1^m P^2_{i(ksp_{n+1})}\right\|}$$

In the equation, $\mathrm{Var}_2(n)$ can indicate the sum of energy value variations between the nth piece of k space data and the preceding and following k space data at each k space location [representing the ith, (i−1)th, and (i+1)th points $P_{i(ksp_n)}$, $P_{i(ksp_{n-1})}$, $P_{i(ksp_{n+1})}$, etc.], and the nth piece of k space data can correspond to the nth piece of image data, that is, sequentially corresponding to the individual offset frequencies with frequency steps. Note that a beneficial effect of choosing to calculate the variations between a plurality of pieces of k space data under the k space (domain) is that doing so can prevent an offset in an image or a movement of the object and can prevent any possible negative impacts of high-frequency signals.

Step S700 is the same as step S60 of the above-described exemplary embodiment, and thus will not be described in detail again herein.

Another aspect of the present disclosure provides a magnetic resonance imaging pre-scan device for magnetic resonance imaging. Referring to FIG. 1, the magnetic resonance imaging pre-scan device comprises: a processor 24 configured to execute a first pulse sequence by means of a magnetic resonance imaging system, acquire, by a radio frequency antenna unit, a plurality of magnetic resonance signals at different offset frequencies at the same location from an object, and record/obtain the corresponding original k space data on the basis of a plurality of magnetic resonance signals; a calculating unit 241 configured to respectively calculate a variation between a plurality of pieces of k space data, and determine, according to the variation, an offset frequency for use as the compensation frequency for compensating for an inhomogeneous magnetic field. Here, the calculating unit 241 is further configured to respectively calculate the sum of amplitude variations or energy value variations at a plurality of k space locations between one piece of first k space data and the first k space data obtained at adjacent offset frequencies.

In some exemplary embodiments, in order that the magnetic resonance imaging pre-scan device may, by analyzing the variation in the image data obtained at different offset frequencies in the image domain, determine an offset frequency for use as the compensation frequency for compensating an inhomogeneous magnetic field, the magnetic resonance imaging pre-scan device further comprises: a reconstruction unit 243 configured to reconstruct the corresponding image data on the basis of the original first k space data, and the calculating unit 241 is further configured to calculate a variation between a plurality of pieces of image data in the image domain, the variation comprising respectively calculating the sum of amplitude variations or energy value variations in a plurality of voxels or pixels between one piece of image data and the image data obtained at adjacent offset frequencies.

In some exemplary embodiments, in order that the magnetic resonance imaging pre-scan device may more efficiently calculate a variation between a plurality of pieces of image data, the processor 24 of the magnetic resonance imaging pre-scan device is further configured to select regions of interest (ROIs) for a plurality of pieces of image data after a plurality of pieces of image data are obtained, so that the calculating unit 241 is configured to calculate variations between a plurality of ROIs in the image domain.

In some exemplary embodiments, the calculating unit 241 of the magnetic resonance imaging pre-scan device is configured to transform the ROI in the image data obtained on the basis of a magnetic resonance signal into the k space to obtain a plurality of pieces of k space data, and calculate the variation between the plurality of k space data in the k space. Here, the variation comprises the sum of amplitude variations or energy value variations in a plurality of k space locations between one piece of k space data and at least two pieces of k space data obtained at adjacent offset frequencies.

In some exemplary embodiments, in order that the magnetic resonance imaging pre-scan device may determine an offset frequency for compensating for an inhomogeneous magnetic field on the basis of a variation between a plurality of pieces of k space data acquired from a pre-scan magnetic resonance signal (including in the image domain or k space), the processor 24 is further configured to determine the minimum variation by comparing the magnitudes of a plurality of variations, so that an offset frequency corresponding to the magnetic resonance signal is selected as the compensation frequency for compensating an inhomogeneous magnetic field.

In some exemplary embodiments, the magnetic resonance imaging pre-scan device further comprises a sequence processor 244, which is configured to construct a first pulse sequence into a plurality of offset frequencies with frequency steps, so that a radio frequency antenna unit receives magnetic resonance signals in sequence.

In some exemplary embodiments, the sequence processor 244 is configured to construct a first pulse sequence so that it comprises a balanced SSFP pulse sequence or a true fast imaging steady state precession pulse sequence.

In some exemplary embodiments, in order that a pulse sequence may be generated on the basis of the offset frequency selected as the compensation frequency for compensating for an inhomogeneous magnetic field, so as to obtain high-quality MR images and offset impacts of an inhomogeneous magnetic field, such as artifacts and distortions, on the MR images, the sequence processor 244 is configured to generate a second pulse sequence, which is executed by means of a magnetic resonance imaging system, so that at least one radio frequency antenna unit responds to the second pulse sequence and the compensation frequency to configure an electrical signal, thus generating a compensated inhomogeneous magnetic field. In some exemplary embodiments, a second pulse sequence generated by the sequence processor 244 may comprise a balanced SSFP pulse sequence or a true fast imaging steady state precession pulse sequence.

Another aspect of the present disclosure provides a computer-readable storage medium on which a program segment readable and operable by the magnetic resonance imaging pre-scan device is stored, so that when the program segment is run by the magnetic resonance imaging pre-scan device, all the steps of the method described above may be executed. Herein, a program segment may comprise software with a source code or implemented software code, wherein the source code has not been compiled and connected or the source code must only be described, and the executable software code only needs to be loaded into a processor for execution. By executing a program segment, the magnetic resonance imaging pre-scan method may be performed quickly and repeatedly by means of the processor. A program segment is configured to enable a processor to implement the method steps according to the present disclosure by means of a processor.

For example, a program segment is stored on a computer-readable storage medium, or on a network or server, from which it is loadable into a processor of the processor, and the processor may be directly connected to the processor, or may be constructed as part of the processor. In addition, control information of a program segment may be stored on an electronically readable data carrier. Control information of an electronically readable data carrier may be designed such that the processor executes a method of the present disclosure when using the data carrier. Examples of electronically readable data carriers include DVDs, hard disks, or mobile hard disks, on which electronically readable control information, especially software, is stored. When the control information is read from the data carrier and stored in the processor, all embodiments of the previously described method according to the present disclosure can be executed.

The present disclosure may further relate to a computer-readable storage medium and/or an electronically readable data carrier on which a program segment readable and implementable by a processor is stored, so that when the program segment is implemented by a processor, all steps of the magnetic resonance imaging pre-scan method are implemented. Realization in the form of software has the advantage that the processor that has been used may be refitted in a simple manner through software update to operate by the method of the present disclosure. In addition to a computer program or program segment, the computer-readable storage medium may comprise additional constituent parts, such as documents and/or additional components, as well as hardware, such as hardware keys for using software, if necessary.

As used herein, "schematic" means "serving as an instance, example or illustration". No drawing or embodiment described herein as "schematic" should be interpreted as a more preferred or more advantageous technical solution.

To make the drawings appear uncluttered, only those parts relevant to the present disclosure are shown schematically in the drawings; they do not represent the actual structure thereof as a product. Furthermore, to make the drawings appear uncluttered for ease of understanding, in the case of components having the same structure or function in certain drawings, only one of these is drawn schematically, or only one is marked.

In this text, "a" does not only mean "just this one"; it may also mean "more than one". As used herein, "first" and "second" etc. are merely used to differentiate between parts, not to indicate their order or degree of importance, or any precondition of mutual existence, etc. In addition, the term "and/or" used in the present disclosure covers any one of the listed items and all possible combinations. For example, A and/or B may mean that A exists independently, A and B exist simultaneously, or B exists independently. In addition, the character "/" used herein generally indicates an "or" relationship between the associated object preceding the character and that following the character.

Although embodiments or examples of the present disclosure have already been described by referring to the drawings, it should be understood that the above-mentioned method, system and device are merely exemplary embodiments or examples, and the scope of the present disclosure is not limited by these embodiments or examples, instead being defined solely by the granted claims and the equivalent scope thereof. Each key element in the embodiments or examples may be omitted or may be replaced by an equivalent key element thereof. In addition, the steps may be performed in a sequence different from that described in the present disclosure. Furthermore, various key elements in the embodiments or examples may be combined in various ways. Importantly, as technology evolves, many key elements described here may be replaced by equivalent key elements appearing after the present disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

10 MR imaging system
11 Magnet
12 Gradient coil unit
13 Radio frequency antenna unit
14 Examination region
15 $B_0$ magnetic field
16 Scanning table
17 Local radio frequency antenna
18 Object
21 Local radio frequency antenna processor
23 Radio frequency antenna processor
24 Processor
241 Calculating unit (calculator)
242 Memory
243 Reconstruction unit (reconstructor)
244 Sequence processor
25 Gradient coil processor
27 output (e.g. display)
28 input
501 Amplitude variation curve
502, 502' Minimum variation
503 Energy value variation curve
505 Image data
701 Region of interest
703 Window

The invention claimed is:

1. A magnetic resonance imaging (MRI) pre-scan method, comprising:
- executing, by MRI system, a first pulse sequence;
- acquiring, by a radio frequency antenna of the MRI system, a plurality of magnetic resonance signals at different offset frequencies at a same location from an object, and recording a plurality of pieces of corresponding first k space data based on the plurality of magnetic resonance signals;

respectively calculating, by a processor of the MRI system, a variation between the plurality of pieces of first k space data, wherein respectively calculating the variation for the plurality of pieces of first k space data comprises:

reconstructing the corresponding image data based on the plurality of pieces of first k space data;

after obtaining a plurality of pieces of image data, selecting regions of interest for the plurality of pieces of image data respectively; and transforming the plurality of regions of interest into k spaces to obtain a plurality of pieces of second k space data, and respectively calculating a variation of the plurality of pieces of second k space data in the k spaces, wherein calculating the variation includes respectively calculating a sum of differences in amplitude values or a sum of differences in energy values at a plurality of k space locations between one piece of second k space data and the second k space data obtained at adjacent offset frequencies;

determining, by the processor and according to the variation, an offset frequency as a compensation frequency for compensating for an inhomogeneous magnetic field; and providing an electronic signal representing the offset frequency as an output of the processor of the MRI system.

2. The method according to claim 1, wherein calculating the variation further comprises respectively calculating a sum of differences in amplitude values or a sum of differences in energy values at a plurality of k space locations between one piece of first k space data and the first k space data obtained at adjacent offset frequencies.

3. The method according to claim 1, wherein respectively calculating the variation between the plurality of pieces of first k space data further comprises:

calculating a variation between a plurality of pieces of image data in an image domain, wherein the calculating the variation between the plurality of pieces of image data in the image domain includes respectively calculating a sum of differences in amplitude values or a sum of differences in energy values in a plurality of voxels or pixels between one piece of image data and the image data obtained at adjacent offset frequencies.

4. The method according to claim 3, wherein the method further comprises, after a plurality of pieces of image data are obtained, respectively selecting regions of interest are selected for the plurality of pieces of image data to calculate a variation in the image domain between the plurality of regions of interest.

5. The method according to claim 1, wherein the first pulse sequence is structured as an offset frequency with a frequency step such that the radio frequency antenna is configured to receive the MR signals in sequence.

6. The method according to claim 1, wherein determining, the offset frequency comprises:

comparing magnitudes of a plurality of variations to determine a minimum variation, and selecting the offset frequency corresponding to the minimum variation as the compensation frequency for compensating for the inhomogeneous magnetic field.

7. The method according to claim 1, wherein the first pulse sequence comprises a balanced Steady State Free Precession (SSFP) pulse sequence or the first pulse sequence comprises a true fast imaging steady state precession pulse sequence.

8. The method according to claim 1, wherein a second pulse sequence is executed by the MRI system, and the radio frequency antenna is configured to give a response to the second pulse sequence and apply the compensation frequency to configure a compensation electronic signal to compensate for the inhomogeneous magnetic field.

9. The method according to claim 8, wherein the second pulse sequence comprises a balanced Steady State Free Precession (SSFP) pulse sequence or a true fast imaging steady state precession pulse sequence.

10. The method according to claim 1, wherein the sum of differences in amplitude values or the sum of differences in energy values is calculated between corresponding k space locations of the one piece of second k space data and the second k space data obtained at adjacent offset frequencies.

11. The method according to claim 1, wherein the sum of differences in amplitude values or the sum of differences in energy values comprises a cumulative sum across the plurality of k space locations.

12. The method according to claim 1, wherein the sum of differences in amplitude values is calculated according to:

$$\mathrm{Var}_1(n) = \frac{1}{2}\left\|\sum_1^m P_{i_{(ksp_n)}} - \sum_1^m P_{i_{(ksp_{n-1})}}\right\| + \frac{1}{2}\left\|\sum_1^m P_{i_{(ksp_n)}} - \sum_1^m P_{i_{(ksp_{n+1})}}\right\|$$

wherein $\mathrm{Var}_1(n)$ indicates the sum of differences in amplitude values between an nth piece of second k space data and preceding and following second k space data at each k space location, and $P_i$ represents points in k space.

13. A magnetic resonance imaging (MRI) system configured to implement the magnetic resonance imaging pre-scan method according to claim 1.

14. A non-transitory computer-readable storage medium with an executable program stored thereon, that when executed, instructs a processor to perform the method of claim 1.

15. A magnetic resonance imaging (MRI) pre-scan device, comprising:

a processor configured to control a MRI system to execute a first pulse sequence; and a radio frequency antenna configured to acquire a plurality of magnetic resonance (MR) signals at different offset frequencies at a same location from an object, and record a plurality of pieces of corresponding first k space data based on the plurality of MR signals, wherein the processor is further configured to;

respectively calculate a variation between the plurality of pieces of first k space data, and data;

reconstruct corresponding image data based on the plurality of pieces of first k space data;

after a plurality of pieces of image data is obtained, select regions of interest for the plurality of pieces of image data;

transform the plurality of regions of interest into k spaces to obtain a plurality of pieces of second k space data; and respectively calculate a variation in the plurality of pieces of second k space data in the k spaces by respectively calculating a sum of differences in amplitude values or a sum of differences in energy values at a plurality of k space locations between one piece of second k space data and the second k space data obtained at adjacent offset frequencies; and determine, according to the variation, an offset frequency as a compensation frequency for compensating for an inhomogeneous magnetic field.

16. The MRI pre-scan device according to claim 15, wherein the processor is further configured to respectively calculate a sum of differences in amplitude values or a sum of differences in energy values at a plurality of k space locations between one piece of first k space data and the first k space data obtained at adjacent offset frequencies.

17. The MRI pre-scan device according to claim 15, wherein the processor is further configured to:

reconstruct the corresponding image data based on the plurality of pieces of first k space data; and calculate a variation between a plurality of pieces of image data in an image domain by respectively calculating a sum of differences in amplitude values or a sum of differences in energy values in a plurality of voxels or pixels between one piece of image data and the image data obtained at adjacent offset frequencies.

18. The MRI pre-scan device according to claim 17, wherein the processor is further configured to, after a plurality of pieces of image data are obtained, select regions of interest for the plurality of pieces of image data, so that the processor calculates a variation between the plurality of regions of interest in the image domain.

19. The MRI pre-scan device according to claim 15, wherein the processor is further configured to compare magnitudes of a plurality of variations to determine a minimum variation, and select the offset frequency corresponding to the minimum variation as a compensation frequency for compensating for the inhomogeneous magnetic field.

20. The MRI pre-scan device according to claim 15, wherein the processor is further configured to construct a first pulse sequence comprising a balanced SSFP pulse sequence or a true fast imaging steady state precession pulse sequence.

21. The MRI pre-scan device according to claim 20, wherein the processor is configured to construct a first pulse sequence comprising an offset frequency with a frequency step, so that a radio frequency antenna receives the magnetic resonance signals in sequence.

22. The MRI pre-scan device according to claim 21, wherein the processor is configured to generate a second pulse sequence such that the radio frequency antenna gives a response to the second pulse sequence and applies the selected compensation frequency to configure an electrical signal to compensate for the inhomogeneous magnetic field.

23. The MRI pre-scan device according to claim 22, wherein the second pulse sequence comprises a balanced SSFP pulse sequence or a true fast imaging steady state precession pulse sequence.

* * * * *